United States Patent
Cumming

(10) Patent No.: US 6,451,056 B1
(45) Date of Patent: Sep. 17, 2002

(54) LENS FOR INCREASED DEPTH OF FOCUS

(76) Inventor: J. Stuart Cumming, 1407 Emerald Bay, Laguna Beach, CA (US) 92651

( * ) Notice: Subject to any disclaimer, the term of this patent is extended or adjusted under 35 U.S.C. 154(b) by 0 days.

(21) Appl. No.: 09/370,235

(22) Filed: Aug. 9, 1999

(51) Int. Cl.[7] ................................................. A61F 2/16
(52) U.S. Cl. ...................... 623/6.18; 623/6.4; 623/6.42; 623/6.44
(58) Field of Search ................ 623/6.37, 6.11, 623/6.13, 6.14, 6.18, 6.22, 6.24, 6.27–6.55, FOR 105

(56) References Cited

U.S. PATENT DOCUMENTS

| | | | | |
|---|---|---|---|---|
| 4,159,546 A | * | 7/1979 | Shearing | 128/898 |
| 4,409,690 A | | 10/1983 | Gess | |
| 4,409,691 A | * | 10/1983 | Levy | 623/6.34 |
| 4,657,546 A | * | 4/1987 | Shearing | 623/6.21 |
| 4,704,123 A | * | 11/1987 | Smith | 623/6.43 |
| 4,743,254 A | * | 5/1988 | Davenport | 623/6.17 |
| 4,892,543 A | * | 1/1990 | Turley | 623/6.13 |
| 5,180,390 A | * | 1/1993 | Drews | 623/6.4 |
| 5,919,230 A | | 7/1999 | Sambursky | |

FOREIGN PATENT DOCUMENTS

| | | | | |
|---|---|---|---|---|
| FR | 2 728 459 A1 | * | 6/1996 | 623/FOR 105 |
| GB | 2 226 246 A | * | 6/1990 | 623/FOR 105 |
| RU | 2034522 C1 | * | 5/1995 | 623/FOR 105 |

* cited by examiner

*Primary Examiner*—David H. Willse
(74) *Attorney, Agent, or Firm*—Fulbright & Jaworski L.L.P.

(57) ABSTRACT

An intraocular lens provides substantially increased depth of focus for accurate near and far vision with an optic much thinner than a natural lens, and the lens being rigid, vaulted posteriorly and adapted for posterior positioning in the capsular bag. The optic is positioned substantially farther from the cornea than a natural lens, so that a cone of light exiting the optic to impinge upon the retina is much smaller than a cone of light from a natural lens. Typically, the optic may be about 1.0 mm thick and its distance from the cornea 7.0–8.0 mm.

25 Claims, 2 Drawing Sheets

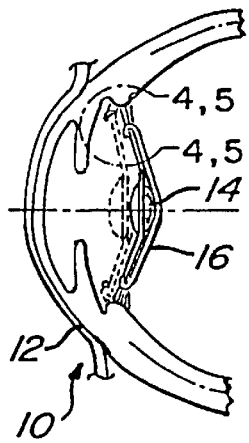
FIG.-1
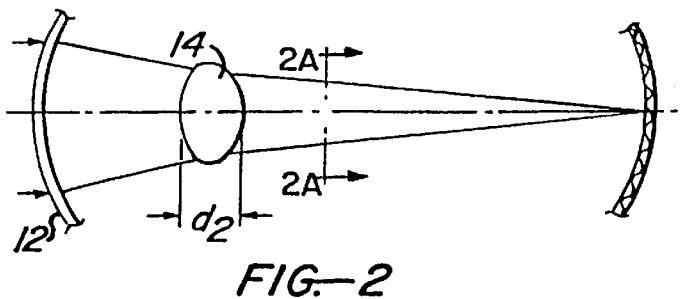
FIG.-2
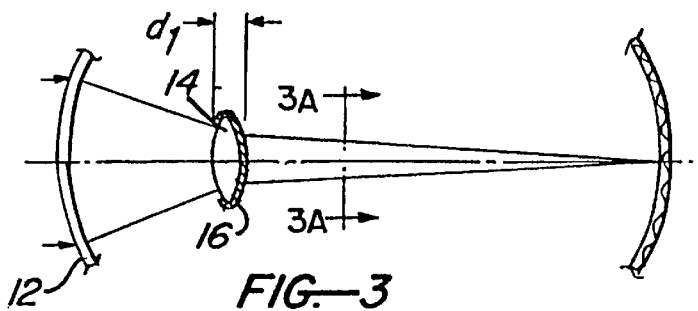
FIG.-3
FIG.-2A
FIG.-3A
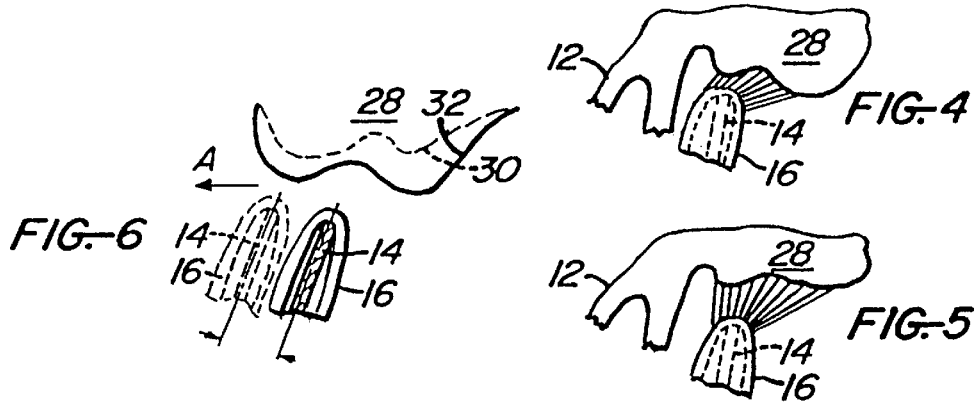
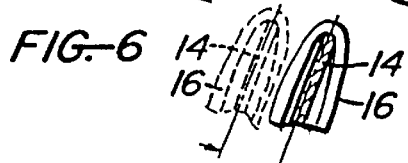
FIG.-6
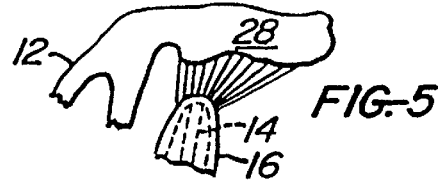
FIG.-4
FIG.-5

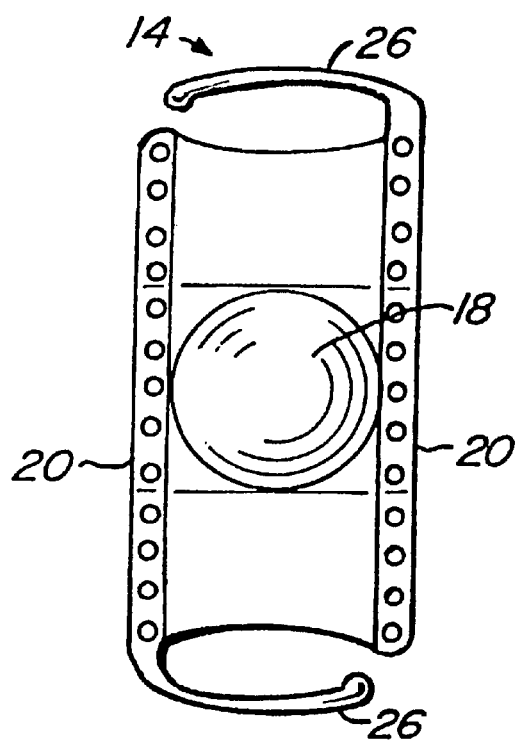
FIG.–7  FIG.–8
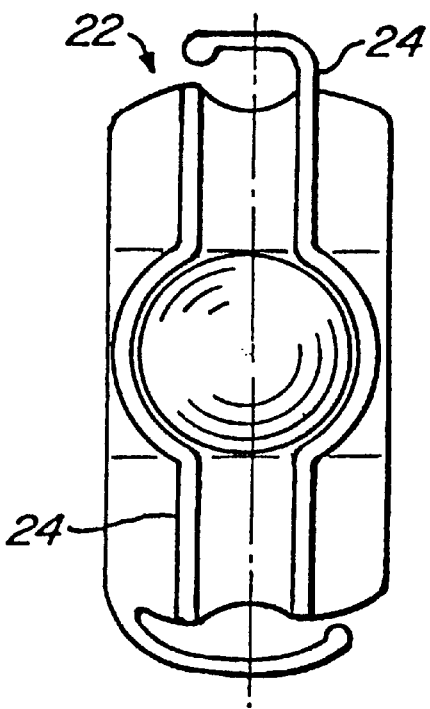
FIG.–9  FIG.–10

LENS FOR INCREASED DEPTH OF FOCUS

BACKGROUND AND SUMMARY OF THE INVENTION

A natural human optic typically has a thickness of about 5.0 mm. Light rays entering the cornea and passing to the optic typically travel about 7.0 to 8.0 mm. Light rays pass from the optic in a cone of light with its apex at the retina. The natural lens provides only a limited degree of depth of focus with clear vision over a limited range of distances.

The present invention provides an optic which is only a fraction the thickness of the natural lens. Whereas the natural lens is about 5.0 mm thick, the lens of the invention may typically be 1.0 mm and may range from about 0.6 mm to 1.5 mm. The distance from the cornea to the optic of the invention is about 7.0–8.0 mm, whereas with a natural lens, the light rays travel only about 3.5 mm from cornea to optic. Light rays refracted by and exiting the optic define a cone of light much smaller in cross-sectional area than the natural lens, and therefore impinge on the retina in a smaller area. The much smaller cone provides greatly increased depth of focus in comparison with a natural lens, and thus enables clear vision over a long range of distances. In effect, the invention provides effective accommodation as between near and far vision, and a person is enabled to view accurately over a wide range of distances. The optic is positioned much farther from the cornea than a natural lens, and this increase of distance minimizes the distance optical power change. The further posterior the optic, the higher the power of the optic and the less movement required for a given power change. The lens according to the invention is rigid, the haptics being rigidly connected to the optic, and the lens is vaulted posteriorly. Thus, the distance between the cornea and the optic is maximized and the distance of travel of light rays between cornea and optic is increased.

The rigid lens causes the optic to move with the periphery of the capsular bag in response to ciliary muscle changes, particularly for near vision.

BRIEF DESCRIPTION OF THE DRAWINGS

FIG. 1 is a cross-sectional view of a frontal portion of a human eye with a lens according to the invention disposed therein;

FIG. 2 is a partial sectional view of an eye showing light rays entering the cornea and exiting the optic in a cone of light from a natural lens to the retina, and FIG. 2A shows a cross-section of the cone of light at the plane 2A—2A of FIG. 2;

FIG. 3 is a view similar to that of FIG. 2, showing an optic according to the invention, and light rays exiting the optic in a cone of light of smaller size than with the natural lens of FIG. 2, and FIG. 3A shows a cross-section of the cone of light of smaller size at the plane 3A—3A of FIG. 3;

FIGS. 4 and 5 are sectional views taken respectively at line 4—4 and line 5—5 in FIG. 1, showing a capsular bag and haptic in relation to the ciliary muscle in near and far vision positions of the capsular bag and haptic;

FIG. 6 is a diagrammatic sectional view of the ciliary muscle and capsular bag showing in solid lines their near vision positions, and showing in broken lines their far vision positions;

FIG. 7 is an elevational view of a preferred embodiment of lens and haptic according to the invention;

FIG. 8 is a side elevational view of the lens of FIG. 7;

FIG. 9 is an elevational view of another preferred embodiment of lens according to the invention; and FIG. 10 is a side elevational view of the lens of FIG. 9.

DESCRIPTION OF THE PREFERRED EMBODIMENTS

The present invention provides substantially increased depth of focus, for effective near and far accurate vision by providing a thin optic which is only a fraction the thickness of a natural lens or a conventional artificial lens optic, and by providing a rigid lens adapted to be positioned posteriorly in the natural capsular bag.

Referring to the drawings, FIG. 1 is a cross-sectional view of an eye 10 with a cornea 12, with a lens 14 according to the invention disposed in the capsular bag 16 of the eye. As indicated in FIG. 2, light rays entering at the cornea are refracted and impact a natural lens 14 which refracts the rays to define a cone of light which impacts the retina. FIG. 3 is a partial sectional view showing a thin optic 18 of the invention disposed substantially farther posteriorly than the natural lens 14 (or a conventional artificial lens) of 5 mm thickness ($d_2$ in FIG. 2). The light rays passing from the cornea to the optic 18 must travel a distance of about 7.0 to 8.0 mm from the cornea to the optic, whereas with the natural lens 14 light rays travel only about 3.5 mm. The light rays refracted by and exiting the optic 18 define a cone of light of much smaller cross-sectional area (FIG. 3A) impact the retina in a smaller area, in comparison with the much larger cone of light and its much larger cross section (FIGS. 2 and 2A). An optic according to the invention may typically be 1.0 mm thick ($d_1$ in FIG. 3), and may range from about 0.5 to about 1.5 mm in thickness.

The much smaller cone of light provides greatly increased depth of focus, thus enabling clear vision over a long range of distances, in comparison with the much larger cone of light produced by the natural human lens or conventional artificial intraocular lens. The much improved depth of focus provides effective accommodation or "pseudo accommodation", as between near arid far vision, so that a person is enabled to view accurately over a wide range of distances. The increase of distance which light rays must travel between the cornea and the optic minimizes the distance optical power change—i.e., the further posterior the optic, the higher the power of the optic and the less movement required for significant power change.

The lens 14 according to the invention is rigid, with the haptics thereof rigidly connected with the optic. The lens is vaulted posteriorly, as shown in FIGS. 1 and 8, in order to maximize the posterior positioning of the optic to increase the distance of travel of light rays between the cornea and the optic. Additional rigidity may be provided by rigid bars 20 secured along the edges of the lens (FIG. 7) or as shown in FIG. 9, a lens 22 may have rigid bars 24 disposed inwardly of the lens edges with arcuate portions extending about the optic, as shown. The haptics are preferably flexible to enable folding for insertion of the lens into the human eye via a slot therein of relatively short length. Lenses according to the invention may preferably embody upper and lower flexible loop portions 26, 26 (FIG. 7) which extend oppositely to facilitate lens rotation during insertion into an eye, without interfering engagement with the capsular bag.

The outer peripheral equator portion of the capsular bag is moved in response to configurational changes in the ciliary muscle as between near and far vision, thereby causing the lens and its optic to move with the periphery of the capsular bag in response to such muscle changes, particularly with respect to near vision. That is, upon contraction of the ciliary muscle, anterior displacement of the capsular bag equator effects corresponding anterior movement of the optic. The lens and optic are free to move anteriorly because of the relative stiffness of the anterior bag resulting from leather-like fibrosis or dead tissue arising from conventional surgical cutting to remove the anterior portion of the bag. The lens is moved posteriorly only when the muscle acts thereon.

FIGS. 4, 5 and 6 are diagrammatic cross-sectional views of the ciliary muscle 28 of the eye in relation to the peripheral or equator portion of the capsular bag with the lens 14 of the invention therein. FIG. 6 shows in broken lines the configuration 30 of the muscle 28 and the relative position of the haptic 14, in a far vision position, and showing in solid lines 32, the muscle configuration 30 and relative position of the haptic for near vision. Muscle configuration indicated at 30 extends into vitreous cavity, thus increasing pressure to a limited degree to further aid in moving the lens anteriorly. Muscle constriction moves the rigid lens forward to a limited degree at the bag periphery, the whole lens moving forwardly.

Thus there has been shown and described a lens for increased depth of focus which fulfills all the objects and advantages sought therefor. Many changes, modifications, variations and other uses and applications of the subject invention will, however, become apparent to those skilled in the art after considering this specification together with the accompanying drawings and claims. All such changes, modifications, variations and other uses and applications which do not depart from the spirit and scope of the invention are deemed to be covered by the invention which is limited only by the claims which follow.

The inventor claims:

1. An intraocular lens for increased depth of focus, comprising:
   a lens body having
      an optic integrally formed with said lens body, said optic with a thickness substantially less than a natural human lens, said optic having an anterior and posterior surface, and
      at least two haptics having an end portion distal to said optic, said haptics anguarly connected with the optic to vault the optic to a maximum posterior position relative to the distal end portions of the haptics,
   wherein at least a portion of said lens body being rigid along a length of said optic,
   wherein said lens body is longitudinally flexible for bending for insertion in an eye,
   wherein the optic is configured to be vaulted to a posterior position and rigidly maintained in a posteriorly vaulted configuration in the capsular bag of the eye during ciliary muscle contraction,
   wherein said optic anterior and posterior surfaces are maintained posteriorly relative to said haptic end portions, and
   whereby light refracted by the cornea travels substantially farther to the optic than with a natural optic and a substantially smaller cone of light passes from the optic to the retina to provide substantially increased depth of focus.

2. A lens according to claim 1, wherein the optic is about 1.0 mm in thickness.

3. A lens according to claim 1, wherein the optic has a thickness between about 0.5 mm and about 1.5 mm.

4. A lens according to claim 1, wherein the lens is rigid and the haptics are rigidly connected with the optic and extend therefrom.

5. A lens according to claim 4, wherein the optic has a thickness between about 0.5 mm and about 1.5 mm.

6. A lens according to claim 4, wherein:
   the rigid lens is adopted to be moved anteriorly for near vision and posteriorly for far vision by changes in ciliary muscle configuration during contraction.

7. A lens according to claim 6, wherein:
   the rigid lens is configured to be moved about 1.0 mm between the anterior near vision and posterior far vision positions, whereby the optic is moved about 1.0 mm between the anterior near vision and posterior far vision positions.

8. A lens according to claim 6, wherein:
   the rigid lens is adapted to be moved anteriorly upon constriction of the ciliary muscle.

9. A lens according to claim 4, further including at least one rigid bar secured substantially adjacent to and extending along at least a portion of the lens.

10. A lens according to claim 9, wherein at least a portion of the rigid bar is substantially adjacent to the optic.

11. A lens according to claim 1, further including at least one rigid bar disposed along a length of the lens body, wherein the rigid bar maintains the lens body in a posteriorly vaulted configuration in the capsular bag of the eye during ciliary muscle contraction.

12. A lens according to claim 1, wherein the angle defined by the angular connection between the optic and the haptics remains substantially constant during ciliary muscle contraction.

13. A lens according to claim 1, wherein the haptics have an outer end extending from the optic and flexible loop portions extend outwardly from the haptic outer end.

14. A lens according to claim 1, wherein the lens body and the optic are foldable.

15. An intraocular lens for increased depth of focus, comprising:
   a lens body having
      an optic integrally formed with said lens body, said optic with a thickness substantially less than the thickness of a natural human lens, said optic having an anterior and posterior surface,
      at least two haptics having an end portional distal to said optic, said haptics rigidly connected to the optic and extending at an the angle therefrom to vault the optic to a posterior position in the capsular bag of the eye, and
      at least one rigid bar extending along the length of the lens body to maintain the lens body in a maximum posteriorly vaulted configuration relative to the distal end portions of the haptics,
   wherein said lens body is longitudinally flexible for banding for insertion in the eye,
   wherein said optic anterior and posterior surfaces are maintained posteriorly relative to said haptic end portions, and
   whereby light refracted by the cornea travels substantially farther to the optic than with a natural human lens and a substantially smaller cone of light passes from the optic to the retina to provide substantially increased depth of focus.

16. A lens according to claim 15, wherein the optic has a thickness between about 0.5 mm and about 1.5 mm.

17. A lens according to claim 15, wherein:
   the lens is adopted to be moved anteriorly for near vision and posteriorly for far vision by changes in ciliary muscle configuration during contraction.

18. A lens according to claim 17, wherein:
   the lens is adapted to be moved anteriorly upon constriction of the ciliary muscle.

19. A lens according to claim 17, wherein:

the lens is configured to be moved about 1.0 mm between the anterior near vision and posterior far vision positions, whereby the optic is moved about 1.0 mm between the anterior near vision and posterior far vision positions.

20. A lens according to claim 15, wherein two rigid bars are disposed in spaced relation and extend longitudinally of the lens.

21. A lens according to claim 15, wherein:

the lens is configured to be moved about 1.0 mm between the anterior near vision and posterior far vision positions, whereby the optic is moved about 1.0 mm between the anterior near vision and posterior far vision positions.

22. A lens according to claim 15, wherein at least a portion of the rigid bar is substantially adjacent to the optic.

23. A lens according to claim 15, wherein the haptics have an outer end extending from the optic and flexible loop portions extend outwardly from the haptic outer end.

24. A lens according to claim 15, wherein the lens body and the optic are foldable.

25. A lens according to claim 16, wherein:

the lens is adopted to be moved anteriorly for near vision and posteriorly for far vision by changes in ciliary muscle configuration during contraction.

* * * * *